United States Patent [19]
Berlhold

[11] 3,936,506
[45] Feb. 3, 1976

[54] PREPARATION OF UNSYMMETRICAL HALOGEN-SUBSTITUTED DIACYL PEROXIDES

[75] Inventor: Robert V. Berthold, South Charleston, W. Va.

[73] Assignee: Union Carbide Corporation, New York, N.Y.

[22] Filed: Feb. 26, 1973

[21] Appl. No.: 335,813

Related U.S. Application Data

[63] Continuation-in-part of Ser. No. 193,717, Oct. 29, 1971, abandoned.

[52] U.S. Cl. .............................................. 260/610 D
[51] Int. Cl.² .................................... C07C 179/14
[58] Field of Search ................................ 260/610 D

[56] References Cited
UNITED STATES PATENTS
1,913,775  6/1933  Straub............................. 260/610 D
3,652,681  3/1972  Wood .............................. 260/610 D FOREIGN PATENTS OR APPLICATIONS
699,768  12/1964  Canada........................... 260/610 D

*Primary Examiner*—Bernard Helfin
*Assistant Examiner*—W. B. Lone
*Attorney, Agent, or Firm*—Bernard Francis Crowe

[57] ABSTRACT

Unsymmetrical halogen-substituted diacyl peroxides have been prepared either by rapidly adding an α-halogen-substituted aliphatic acyl halide and a hydrocarbon solvent to an aqueous solution of an alkali metal peroxide followed by portion-wise addition of an acyl halide or by rapidly adding an acyl halide and a hydrocarbon solvent to an aqueous solution of an alkali metal peroxide followed by portion-wise addition of an α-halogen-substituted aliphatic acyl halide. The formation of diacyl peroxides and symmetrical halogenated diacyl peroxides as by-products is minimized by either technique.

14 Claims, 1 Drawing Figure

COMPARATIVE HALF-LIFE CURVES AT 45°C

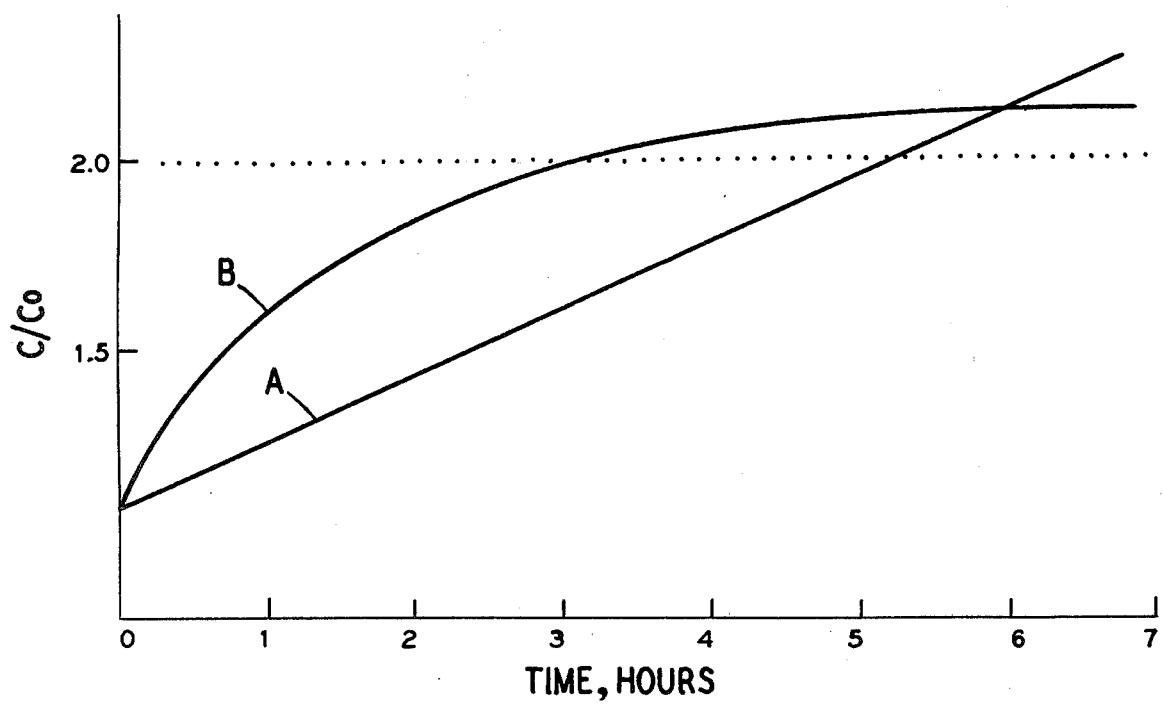

PREPARATION OF UNSYMMETRICAL HALOGEN-SUBSTITUTED DIACYL PEROXIDES

This is a continuation-in-part of Ser. No. 193,717 filed Oct. 29, 1971 now abandoned.

BACKGROUND OF THE INVENTION

This invention pertains to a method of preparing unsymmetrical halogen-substituted diacyl peroxides and in particular to the preparation of unsymmetrical bromo-or chloro- substituted diacyl peroxides.

Unsymmetrical halogen substituted diacyl peroxides have been prepared by adding approximately equimolar quantities of two dissimilar acyl chlorides dissolved in an inert solvent to an excess of aqueous sodium peroxide solution. However, this procedure affords a mixture of peroxides of which the desired unsymmetrical peroxide constitutes a much smaller percentage than is obtained by the process of this invention. The other components of such a procedure are the symmetrical halogen substituted diacyl peroxide and the unhalogenated symmetrical diacyl peroxide. This reaction is delineated in the equation below:

where $a$, $b$ and $c$ represent quantities which vary according to the reactivities of the starting acyl halides; and R is a long chain alkyl radical.

It is an object of this invention to provide a means for obtaining a high yield of unsymmetrical diacyl peroxides with a substantial reduction in contamination from symmetrical diacyl peroxides of either the halogen substituted or non-halogen substituted types:

It is another object of this invention to provide unsymmetrical halogenated acyl peroxides having about 12 to 18 carbon atoms on each side of the molecule.

Other objects will become apparent to those skilled in the art upon reading the specification.

SUMMARY OF THE INVENTION

A method of preparing unsymmetrical α-halogen substituted diacyl peroxides having the formula:

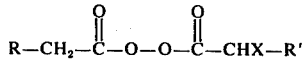

wherein each of R and R' is a long chain alkyl radical having about 10 to about 16 carbon atoms and X is a halogen selected from the group consisting of bromine and chlorine, has been developed which comprises the steps of:

a. agitating an aqueous solution of an alkali metal peroxide at about 0 to about 10°C.;
b. adding a normally liquid hydrocarbon solvent to the agitated solution of (a) while maintaining a temperature of about 0° to about 10°C.;
c. rapidly adding about 1 mol of an α-halogen substituted aliphatic acyl halide having about 12 to about 18 carbons therein;
d. agitating the mixture of (a), (b) and (c) for at least about 2 hours at about 0° to about 10°C.;
e. adding about 1 mol of an aliphatic acyl halide having about 12 to about 18 carbon atoms therein in small regular increments to the agitated mixture of (a), (b) and (c) while continuing agitation for at least about 0.5 hours at a temperature of about 0° to about 10°C.;
f. lowering the pH of the agitated mixture of (a), (b), (c) and (e) to about 1 to 1.5 by acidification of said agitated mixture of (a), (b), (c) and (e);
g. allowing the resultant reaction mixture to stand unagitated until said reaction mixture separates into an hydrocarbon solution layer and an aqueous layer; and
h. isolating the hydrocarbon solution layer containing unsymmetrical α-halogen substituted diacyl peroxide.

This method provides a mixture containing predominantly the unsymmetrical peroxide and greatly minimizes the formation of the symmetrical peroxides. The novel feature of this process resides in the in situ conversion of the contained symmetrical bis α-haloacyl peroxide to the α-halogen-substituted aliphatic peracid alkali metal salt prior to its subsequent reaction with acyl halide.

An alternate method of preparing unsymmetrical α-halogen substituted diacyl peroxides having the formula:

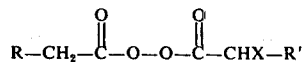

wherein each of R and R' is a long chain alkyl radical having about 10 to about 16 carbon atoms and X is a halogen selected from the group consisting of bromine and chlorine, has been developed which comprises the steps of:

A. agitating an aqueous solution of an alkali metal peroxide at about 0° to about 10°C.;
B. adding a normally liquid hydrocarbon solvent to the agitated solution of (A) while maintaining a temperature of about 0° to about 10°C.;
C. rapidly adding about 1 mol of an aliphatic acyl halide having about 12 to about 18 carbons therein;
D. agitating the mixture of (A), (B) and (C) for at least about 2 hours at about 0° to about 10°C.;
E. adding about 1 mol of an α-halogen substituted aliphatic acyl halide having about 12 to 18 carbons therein in small regular increments to the agitated mixture of (A), (B) and (C) while continuing agitation for at least about 0.5 hours at a temperature of about 0° to about 10°C.;
F. lowering the pH of the agitated mixture of (A), (B), (C) and (E) to about 1 to 1.5 by acidification of said agitated mixture of (A), (B), (C) and (E);
G. allowing the resultant reaction mixture to stand unagitated until said reaction mixture separates into an hydrocarbon solution layer and an aqueous layer; and
H. isolating the hydrocarbon solution layer containing unsymmetrical α-halogen substituted diacyl peroxide.

DESCRIPTION OF THE INVENTION

The aqueous solution of alkali metal peroxide used in the first step of this invention can be conveniently prepared by mixing an aqueous solution of hydrogen peroxide with an alkali metal hydroxide. For convenience and economic reasons sodium hydroxide is the preferred hydroxide although potassium or lithium hydroxide may be used as well.

The selection of normally liquid hydrocarbon solvent used in the second step is not narrowly critical. Aliliphatic hydrocarbons, such as hexane, heptane and the like; halogenated aliphatic hydrocarbons such as methylene chloride, ethylene dichloride, n-butyl chloride, and the like, and substituted aromatic hydrocarbons such as toluene, ortho-xylene, metaxylene, ethylbenzene and the like may be advantageously used. The choice of solvent will also be dictated to some extent by the requirement that it be a liquid at 0°C. The hydrocarbon solvent should also be free of groups which would be reactive with either sodium hydroxide, acyl halides and/or the peroxide formed as the final product, that is the unsymmetrical α-halo acyl peroxide.

Any type of agitation known to those skilled in the art, such as, stirring, can be used.

Pressure is not critical but it is preferred to employ atmospheric conditions for economical reasons although superatmospheric as well as subatmospheric pressures can be used if desired.

Although reaction temperatures in the range of about 0° to about 10°C. can be used, it is preferred in the first method to use a range of about 0° to about 5°C. for the reaction between alkali metal peroxide and the α-halogen substituted acyl halide which produces an alpha halogen substituted aliphatic peracid alkali metal salt according to the equation shown below:

(1) 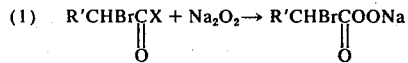

where x is bromine or chlorine and R' is an alkyl group having about 10 to 16 carbon atoms.

Even though time is not narrowly critical for the formation of the α-halogen substituted aliphatic peracid alkali metal salt as shown above, it is preferred to allow this reaction to proceed at least 2 hours in order to insure maximum yields. It is even more preferred to use a reaction time of about 3 to 4 hours. This step can be extended beyond 4 hours but there is a gradual decrease in yield as one exceeds this upper limit.

The addition of the acyl halide to the α-halogen substituted peracid alkali metal salt is preferably done in small regularly timed increments to minimize formation of unsymmetrical symmetrical peroxide. The volume of these increments depends on the total volume of the reactants used in any one run.

The preferred temperature of addition of the acyl halide is the same as that for the preparation of the α-halogen substituted peracid alkali metal salt.

It is preferred to continue stirring the reaction mixture after the addition of acyl halide is complete for about 30 minutes although this time is by no means critical.

The acidification of the reaction mixture is desirable since it precludes the formation of alkali metal carboxylates which act as emulsifiers and make the separation of the aqueous from the hydrocarbon layer more difficult. Any commonly used acids can be used for this purpose although it is preferred to use mineral acids such as sulfuric acid or hydrochloric acid.

The preferred peroxides made by this invention are 2-bromolauroyl lauroyl peroxide and 2-chlorolauroyl lauroyl peroxide because of the combination of availability and effectiveness for initiating polymerization of vinyl monomers.

It is also preferred to isolate the α-halogen substituted unsymmetrical peroxide as a solution in hydrocarbon solvent since this is a convenient way of handling this material as an initiator for polymerization.

As will be discussed in more detail infra, the purity of the peroxide initiator made by the abovedescribed methods affords a smoother polymerization reaction for the polymerization of vinyl monomers than previously used methods in which a mixture of peroxides was obtained. This is due to the more constant decomposition range resulting from the greatly increased relative concentration of the unsymmetrical peroxide species.

In the second or alternate method the process variables recited above also hold true. Thus for the reaction between alkali metal peroxide and acyl halide, the reaction temperature can be between about 0 to 10°C. although a range of about 0° to 5°C. is preferred. The equation for this reaction is:

(2) 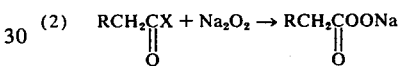

where x is bromine or chlorine and R is an alkyl group having about 10 to 16 carbon atoms.

The more preferred time allowed for the formation of the unsubstituted aliphatic peracid alkali metal salt in (2) is also about 3 to 4 hours, although again this is not critical.

The addition of α-halogen substituted acyl halide to the unsubstituted aliphatic peracid alkali metal salt is also preferably done in small regularly timed increments at a temperature of about 0° to about 10°C.

The invention is further described in the examples which follow. All parts and percentages are by weight unless otherwise specified.

EXAMPLE 1

Preparation of 2-bromolauroyl lauroyl peroxide

A solution of sodium peroxide prepared by the addition of 15.7 grams of 47.8 percent hydrogen peroxide to 17.6 grams of sodium hydroxide dissolved in 175 ml. of water was stirred in a 3 necked round-bottom flask equipped with stirrer, thermometer and an addition funnel at 0°C. while 70.6 grams of a mixture containing 80 percent α-bromolauroyl halide (a mixture of α-bromolauroyl chloride and of α-bromolauroyl bromide) and 20% lauroyl chloride dissolved in 200 grams of toluene was rapidly added. The resulting mixture was stirred at 0°C. for 4 hours whereupon 43.2 grams of lauroyl chloride was added dropwise. After stirring for about 35 minutes at 0°C. the pH of the reaction mixture was observed to have dropped from 14 to 6. At this point 9 grams of a 20 percent aqueous solution of sulfuric acid was added dropwise causing the pH of the mixture to be lowered to about 1.0–1.5. The reaction mixture was transferred to a separatory funnel and placed in a crushed ice bath. After standing for about 30 minutes, the layers were separated and the upper toluene solution layer was found to contain 29.3 percent peroxide calculated as 2-bromolauroyl lauroyl peroxide. This represented a yield of 86.2 percent based on either α-bromolauroyl bromide or lauroyl chloride. The assay of the 2-bromolauroyl lauroyl peroxide was carried out iodometrically. The method used employed a 0.001 percent solution of ferric chloride hexahydrate dissolved in glacial acetic acid to insure complete decomposition of the diacyl peroxide. This method is described by L. S. Silbert and D. Swern in the Journal of the American Chemical Society, Volume 81, page 2364 (1959). The half-life at 45°C. of the mixture containing predominantly 2-bromolauroyl lauroyl peroxide was about 5 hours as compared to a half-life of about 6 hours for pure 2-bromolauroyl lauroyl peroxide when measured under identical conditions. Half-lives were determined by taking samples containing approximately 30 percent diacyl peroxide dissolved in toluene weighed into pressure bottles which contain chloroform, to provide solutions containing 1.5 percent diacyl peroxide. After a purge with nitrogen the bottles were capped and exposed to 45°C. temperature in a constant temperature bath for varying cooled of time. At one hour intervals samples were withdrawn, colled to room temperature, uncapped and treated successively with a saturated solution of sodium iodide and 0.001 percent solution of ferric chloride hexahydrate dissolved in glacial acetic acid. After standing in the dark for 15 minutes, water was added and the sample titrated until free of color with a standardized solution of sodium thiosulfate. The halflife is defined as the time required for the decomposition of one-half of the initial amount of peroxide present. The decomposition of diacyl peroxides is a first order reaction. As such, the first order kinetic expression for the rate of disappearance of species, A, at constant temperature is applicable. This may be expressed as:

$$-\frac{dc_A}{dt} = kC_A$$

or
$$C_o = Ce^{-kt}$$
which can also be written $$\log(C/C_o) = \frac{kt}{2.303}$$

where
C = initial concentration,
$C_o$ = concentration at time $t$, and
$k$ = rate constant, in units of $t^{-1}$.

EXAMPLE 2

Example 1 was repeated with the exception that the α-bromoauroyl halide mixture was replaced by α-chlorolauroyl chloride. Comparable yields of α-chlorolauroyl lauroyl peroxide were obtained. The halflife of this product was about 3.5 hours at 40°C.

CONTROL

A solution prepared by the addition of 2.72 grams of 50 percent hydrogen peroxide to 3.2 grams of sodium hydroxide dissolved in 50 ml. of water was stirred in a round bottom 3-necked flask equipped with a stirrer, thermometer and an addition funnel and cooled to 0°C., keeping the temperature at 0°C. to −5°C. A mixture of 6.3 grams of lauroyl chloride and 16.7 grams of α-bromolauroyl bromide (which contains 23 percent lauroyl chloride) was rapidly added next, dropwise. The mixture was stirred for an additional hour and then 34 grams of toluene was added and the mixture stirred at 0° to −5°C. for an additional 10 minutes. The layers were then separated and the toluene layer washed with ice water. After drying over anhydrous sodium sulfate the toluene layer was filtered and analyzed for peroxide. It was found to contain 31.8 percent peroxide calculated at 2-bromolauroyl lauroyl peroxide. The yield was 85.5 percent but as can be seen from an examination of the Figure, the peroxide product is contaminated with bis-2-bromolauroyl peroxide. The vertical axis of the graph in the Figure, $C/C_o$, represents the initial concentration of the peroxide mixture divided by the observed concentration of the mixture at a given time exposure at 45°C., plotted on a logarithmic scale. The 2.0 point on this axis represents the point at which one-half of the peroxide has been consumed by the peroxide determination described supra. The horizontal axis is linear and depicts the time in hours. Line A representing the decomposition of the product from Example 1 shows that the 2-bromolauroyl lauroyl peroxide sample is decomposing by simple first-order kinetics. Line B, representing the decomposition of the product from the Control, on the other hand, shows a much more rapid decomposition at the earlier exposure times with a flattening of the curvve as the exposure time increases. This indicates the presence of bis-2-bromolauroyl peroxide which decomposes first. The flattening of the curve indicates the presence of unsymmetrical 2-bromolauroyl lauroyl peroxide, the desired product, in reduced amounts because some of the α-bromolauroyl halide needed to make it was consumed in the formation of bis-2-bromolauroyl peroxide. As the curve continues it remains flat because of the second impurity, dilauroyl peroxide, also present in the product mix from the Control, since dilauroyl peroxide has a half-life of well over 100 hours at 45°C.

The undesirability of this peroxide mix for use in initiating the polymerization of vinyl monomer resides in the fact that in the earlier stages of polymerization vigorous exothermic reactions occur and then the initiator lags behind the desired rate. The ideal initiator is one which decomposes at a constant rate which requireS a higher degree of purity. The Figure demonstrates the higher purity of the unsymmetrical halogen substituted acyl peroxide provided by the claimed invention.

EXAMPLE 3

When Example 1 is repeated with the exception that α-chlorostearoyl chloride and stearoyl chloride are used as the reactants, comparable yields of 2-chlorostearoyl stearoyl peroxide are obtained.

Although the invention has been described in its preferred form with a certain degree of particularity, it is understood that the present disclosure has been made only by way of example, and that numerous changes can be made without departing from the spirit and scope of the invention.

What is claimed is:

1. A method of preparing unsymmetrical α-halogen substituted diacyl peroxides having the formula:

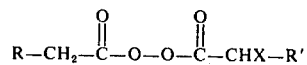

wherein each of R and R' is a long chain alkyl radical having about 10 to about 16 carbon atoms and X is a halogen selected from the group consisting of bromine and chlorine, which comprises the steps of:

a. agitating an aqueous solution of an alkali metal peroxide at about 0° to about 10°C.;
b. adding a hydrocarbon solvent which is liquid at 0°C. to the agitated solution of (a) while maintaining a temperature of about 0° to about 10°C.;
c. rapidly adding about 1 mol of an α-halogen substituted aliphatic acyl halide having about 12 to about 18 carbons therein;
d. agitating the resultant mixture of (a), (b) and (c) for at least about 2 hours at about 0° to about 10°C.;
e. adding about 1 mol of an aliphatic acyl halide having about 12 to 18 carbon atoms therein in small regular increments to the agitated mixture of (d) and continuing agitation for at least 0.5 hours at a temperature of about 0° to about 10°C.;
f. lowering the pH of the agitated mixture of (e) to about 1 to 1.5 by acidification of said agitated mixture of (e);
g. allowing the resultant reaction mixture to stand unagitated until said reaction mixture separates into a hydrocarbon solution layer and an aqueous layer; and
h. isolating the hydrocarbon solution layer containing unsymmetrical halogen substituted diacyl peroxide.

2. Method claimed in claim 1 wherein R and R' are each 10 and X is chlorine.
3. Method claimed in claim 1 wherein R and R' are each 10 and X is bromine.
4. Method claimed in claim 1 wherein R and R' are each 16 and X is bromine.
5. Method claimed in claim 1 wherein R and R' are each 16 and X is chlorine.
6. Method claimed in claim 1 wherein the hydrocarbon solvent is toluene.
7. Method claimed in claim 1 wherein the alkali metal peroxide is sodium peroxide.
8. A method of preparing unsymmetrical α-halogen substituted diacyl peroxides having the formula:

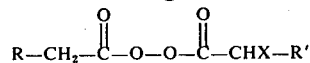

wherein each of R and R' is a long chain alkyl radical having about 10 to about 16 carbon atoms and X is a halogen selected from the group consisting of bromine and chlorine, which comprises the steps of:

A. agitating an aqueous solution of an alkali metal peroxide at about 0° to about 10°C.;
B. adding a hydrocarbon solvent which is liquild at 0°C. to the agitated solution of (A) while maintaining a temperature of about 0° to about 10°C.;
C. rapidly adding about 1 mol of an aliphatic acyl halide having about 12 to about 18 carbons therein;
D. agitating the resultant mixture of (A), (B), and (C) for at least about 2 hours at about 0° to about 10°C.;
E. adding about 1 mol of an α-halogen substituted aliphatic acyl halide having about 12 to 18 carbons therein in small regular increments to the agitated mixture of (D) while continuing agitation for at least about 0.5 hours at a temperature of about 0° to about 10°C.;
F. lowering the pH of the agitated mixture of (E) to about 1 to 1.5 by acidification of said agitated mixture of (E);
G. allowing the resultant reaction mixture to stand unagitated until said reaction mixture separates into an hydrocarbon solution layer and an aqueous layer; and
H. isolating the hydrocarbon solution layer containing unsymmetrical α-halogen substituted diacyl peroxide.

9. Method claimed in claim 8 wherein R and R' are each 10 and X is chlorine.
10. Method claimed in claim 8 wherein R and R' are each 10 and X is bromine.
11. Method claimed in claim 8 wherein R and R' are each 16 and X is chlorine.
12. Method claimed in claim 8 wherein R and R' are each 16 and X is bromine.
13. Method claimed in claim 8 wherein the hydrocarbon solvent is toluene.
14. Method claimed in claim 8 wherein the alkali metal peroxide is sodium peroxide.

* * * * *